Nov. 26, 1935. F. H. HOWARD Plant Pat. 149
ROSE
Filed Feb. 4, 1935
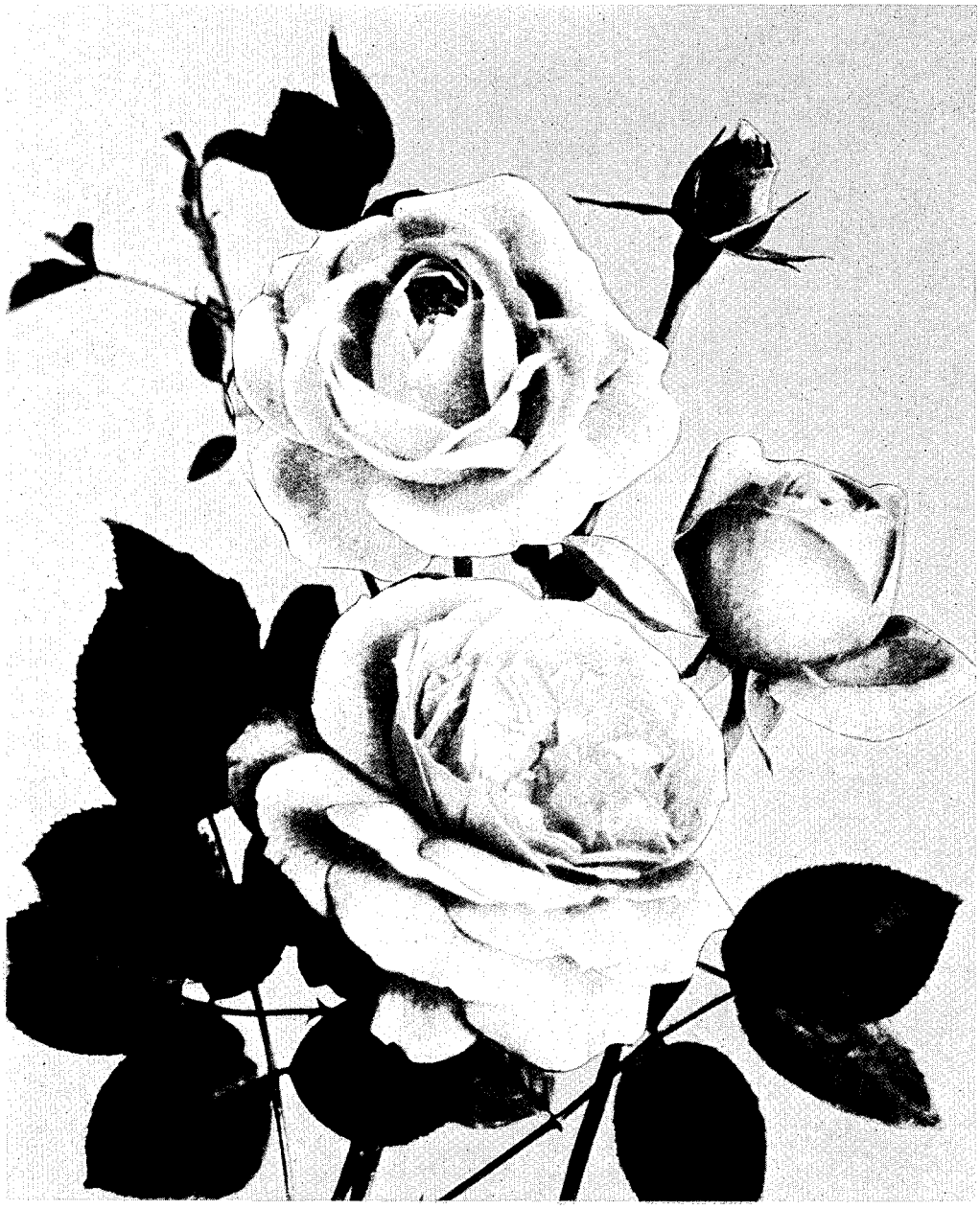
INVENTOR
Frederick Huber Howard
By Orville M. Kile
PLANT PATENT AGENT Patented Nov. 26, 1935

Plant Pat. 149

UNITED STATES PATENT OFFICE

149

ROSE

Frederick Huber Howard, Montebello, Calif., assignor to Henry A. Dreer, Incorporated, Philadelphia, Pa., a corporation of New Jersey Application February 4, 1935, Serial No. 4,967

1 Claim. (Cl. 47—61)

My present invention relates to improvements in fragrant hybrid tea roses. The object of this invention is to provide a new and distinct variety of rose of the type mentioned, having desirable and pleasing color qualities as well as desirable growing and flowering characteristics inherited from its polyantha ancestor. More specifically my invention consists of the production of a new and distinct variety of rose of the fragrant hybrid tea type having a distinctive bright red color (Tyrian Rose to Rose Red, Plate XII, Ridgway's Color Standards and Nomenclature), having free-flowering habits, long-lasting qualities of blossom, and other desirable and valuable characteristics. This is in fact a new race of roses combining the size of bush and flower and length of stem of the hybrid tea type, with the free flowering habits of the polyantha type.

This new variety was developed by crossing a seedling from the E. G. Hill variety (seedling numbered 72) and an unnamed large flowered polyantha variety.

The accompanying illustrations show in full natural color in the fall of the year and in the vicinity of Philadelphia, a tightly rolled bud, three blossoms in various stages of development, and a quantity of foliage.

The following is a detailed description of this rose plant and flower which has been asexually reproduced and its characteristics found definitely fixed.

*The plant*—usually attains a height of about 36 inches under normally good conditions. It is an exceedingly strong grower and very floriferous. The flowers are nearly always borne singly on long stems which make them suitable for cut flower use as well as for garden decorative use.

*Foliage.*—Moderately plentiful; leaves Hellebore Green in color (Plate XVII, Ridgway's Color Standards and Nomenclature), except that the tips of the newest growth at some seasons are coppery in color. Leaves are medium to small in size, rounded rather than elongated in shape, having finely serrated edges. The raches of the compound leaves are free of thorns.

*Stems.*—Rather heavy below the peduncle and only slightly zig-gagged in shape. They are almost entirely free of thorns. The peduncle is frequently tinted with a reddish-brown color particularly in field grown specimens. Ordinarily the peduncle is a lighter green than the leaves.

*Stipules.*—Narrow and terminating in rather sharp non-curling points.

*Sepals.*—Short and not given to foliaceous development although having numerous small side spurs or branches.

*Buds.*—Short and compact, assuming a globular shape when half opened.

*Blossoms.*—Notably flat across the top when half to three-fourths open. This variety is much given to opening in the form of three or four whorls of central petals which fill the central part of the flower. One or two rows of the outer petals turn back fully at an early stage in the opening of the flower but the remaining petals retain the cupped form until the flower is well advanced toward maturity.

In early November, field-grown specimens in the vicinity of Philadelphia have about 44 petals of medium size. Each petal is somewhat more rounded than the usual rose petal type.

The color which is best described as between Tyrian Rose and Rose Red (Plate XII, Ridgway's Color Guide) is rather uniformly distributed over the inside surface of the petals. The outer surfaces are, however, somewhat lighter in color through the central and basal portions. A very small yellow to chrome spot is found on each petal at the point of attachment.

This rose does not turn purple or blue with age.

*Fragrance*—has a faint fruity odor.

*Stamens.*—Numerous, yellowish in color and mounted by large, flat, buff anthers having large dark centers.

*Pistils.*—Numerous, light colored.

*Comparisons*

This new variety is notably different from the varieties Charles E. Douglass and Lieutenant Chaure in its shorter, chunkier bud, and from E. G. Hill by its more regular form and somewhat deeper color. There are, however, many other points of difference.

I claim:—

The new variety or type of rose plant herein described and illustrated characterized particularly by its profuse production of blossoms of a distinctive Tyrian Rose to Rose Red color, as illustrated, the absence of thorns, the size and shape of leaf and by the long-lasting qualities of its flowers with freedom from bluing with age.

FREDERICK HUBER HOWARD.